US005618672A

United States Patent [19]

Stodola et al.

[11] Patent Number: 5,618,672

[45] Date of Patent: Apr. 8, 1997

[54] METHOD FOR ANALYZING PARTIAL GENE SEQUENCES

[75] Inventors: Robert K. Stodola, Flourtown; Frank L. Tobin, Broomall; Arthur L. Williams, Jr., Bethlehem, all of Pa.

[73] Assignee: SmithKline Beecham Corporation, Philadelphia, Pa.

[21] Appl. No.: 459,899

[22] Filed: Jun. 2, 1995

[51] Int. Cl.$^6$ .............................. C12Q 1/68; G06F 15/18
[52] U.S. Cl. ................................................. 435/6; 395/13
[58] Field of Search ................................... 435/6; 395/13

[56] References Cited

PUBLICATIONS

Adams et al., "Complementary DNA Sequencing: Expressed Sequence Tags and Human Genome Project", *Science* 252, pp. 1651–1656 (1991).

E.W. Myers, "Advances in Sequence Assembly" pp. 231–248 from Automated DNA Sequencing and Analysis, Adams et al. eds., Academic Press (1994).

Kececioglu et al., "Combinaortial algorithms for DNA sequence Assembly" *Algorithmica* 13, pp. 7–51 (1995).

Xiaoqiu Huang, "A Contig Assembly Program Based on Sensitive Detection of Fragment Overlaps", *Genomics* 14, pp. 18–25 (1992).

"Fragment Assembly" chapter from GCG Package Manual, pp. 3–4 to 3–48, ©1994 Genetics Computer Group, Inc.

Xiaoqiu Huang, "On global sequence alignment", *Cabios* 10, pp. 227–235 (1994).

Huang et al., "A space-efficient algorithm for local similarities", *Cabios* 6, pp. 373–381 (1990).

Huang et al., "Parallelization of a local similarity algorithm", *Cabios* 8, pp. 155–165 (1992).

Xiaoqiu Huang, "An algorithm for identifying regions of a DNA sequence that satisfy a content requirement", *Cabios* 10, pp. 219–255 (1994).

Gleizes et al., "A global approach for contig construction," *Cabios* 10, pp. 401–408 (1994).

Zhang et al., "An algorithm based on graph theory for the assembly of contigs in physical mapping of DNA", *Cabios* 10, pp. 309–317 (1994).

Peltola, et al., "SEQAID: a DNA sequence assembling program based on a mathematical model", *Nucleic Acids Research* 12, pp. 307–321 (1984).

Michael Waterman, "Sequence Alignments", pp. 53–92 in Mathematical Methods for DNA Sequences, CRC Press (1989).

Michael Waterman, "Consensus Patterns in Sequences", pp. 93–115 in Mathematical Methods for DNA Sequences, CRC Press (1989).

Karlin et al, "Patterns in DNA and Amino Acid Sequences and their Statistical Signficance", pp. 133–157 in Mathematical Methods for DNA Sequences, CRC Press (1989).

Smith et al., Nucleic Acids Research 13(2):645–656. 1985.

*Primary Examiner*—Douglas W. Robinson
*Assistant Examiner*—Thanda Wai
*Attorney, Agent, or Firm*—Kirk Baumeister; Edward T. Lentz

[57] ABSTRACT

An computer-based iterative method for analyzing partial gene sequences. Putative gene assemblies are built from partial gene sequences by the method. A series of pre-processing steps prior to assembly allows efficient and accurate assembly of large amounts of partial gene sequences.

10 Claims, 1 Drawing Sheet

METHOD FOR ANALYZING PARTIAL GENE SEQUENCES

FIELD OF THE INVENTION

This invention relates to a computer-based method for building putative gene assemblies from partial gene sequences.

BACKGROUND OF THE INVENTION

The human genome is estimated to contain 3 billion base pairs of DNA. Within the genome, it is believed that approximately 50,000 to 100,000 gene coding sequences are dispersed. The gene sequences are thought to represent about 3% or approximately 90 million base pairs of the human genome.

It is generally recognized that elucidation of the structure of all human genes and their organization within the genome will be beneficial to the advancement of medicine and biology. Databases such as the Genome Sequence Data Bank and GenBank serve as repositories of the nucleotide sequence data generated by ongoing research efforts. Despite the efforts to date, GenBank lists the sequences of only a few thousand human genes.

Recent advances in automated, large-scale sequencing techniques have led to the initiation of two broad approaches to obtaining the sequence of the human genome. While scientific debate continues as to the best approach, chromosome mapping and sequencing and cDNA sequencing projects have begun in earnest.

The Human Genome Initiative, a multinational effort having government backing in the United States and other countries, is attempting to characterize the genomes of humans and other model organisms on a chromosomal approach. In the private sector, large-scale sequencing of cDNA reverse transcribed from mRNA expressed in various human tissues, cell types and developmental stages is being pursued by a number of entities.

After publication of the Maxam-Gilbert and Sanger et al. nucleotide sequencing techniques, manual gene sequence assembly methods were practical for single gene or viral genome sequencing projects. As sequencing projects became more ambitious, manual techniques could be supplemented by computer-assisted sequence assembly where overlaps between fragments were identified by software rather than by eye. However, the large scale of DNA sequencing projects and the rapidity with which sequence data is generated by automated sequencer machines has resulted in data analysis becoming a rate-limiting step in assembly of gene sequence data. The volume of data being generated by large-scale sequencing projects requires automated analysis in order to provide assembled sequence data in a timely manner.

Towards this end, efforts have been made to improve computer-assisted assembly of nucleotide sequence data. For example, in "Automated DNA Sequencing and Analysis", Adams et al. eds., Academic Press (1995), E. W. Myers presents a discussion of software systems for fragment assembly in Chapter 32, while S. Honda et al. describe in Chapter 33 the Genome Reconstruction Manager, a long-term software engineering project to develop a system to support large-scale sequencing efforts.

Despite these efforts, a need exists for improvements over existing methods. The improved methods will provide computer-assisted nucleotide sequence assembly methods capable of more accurately and more efficiently assembling large amounts of sequence data.

SUMMARY OF THE INVENTION

Accordingly, one aspect of the present invention is a computer-based method for analyzing partial gene sequences. A computer-based iterative method for building putative gene assemblies from a plurality of partial gene sequences is provided. The method allows for the incremental addition of new partial gene sequences to be integrated with an existing plurality of putative gene assemblies. The method comprises preprocessing of the partial gene sequences and existing putative gene assemblies and assembling, responsive to grouping relationships, a consensus sequence from the preprocessed partial gene sequences and putative gene assemblies. Preprocessing comprises the steps of annotating regions within each of the plurality of partial gene sequences and each of the plurality of existing putative gene assemblies; and grouping annotated partial gene sequences with other annotated partial gene sequences, where the other annotated partial gene sequences include components of the existing plurality of putative gene assemblies. Preprocessing allows for efficient and accurate assembly.

BRIEF DESCRIPTION OF THE DRAWING

The accompanying drawing, which is incorporated in and constitutes a part of the specification, illustrates a preferred embodiment of the invention and together with the description serves to explain the principles of the invention.

DETAILED DESCRIPTION OF THE PREFERRED EMBODIMENTS

Figure 1:
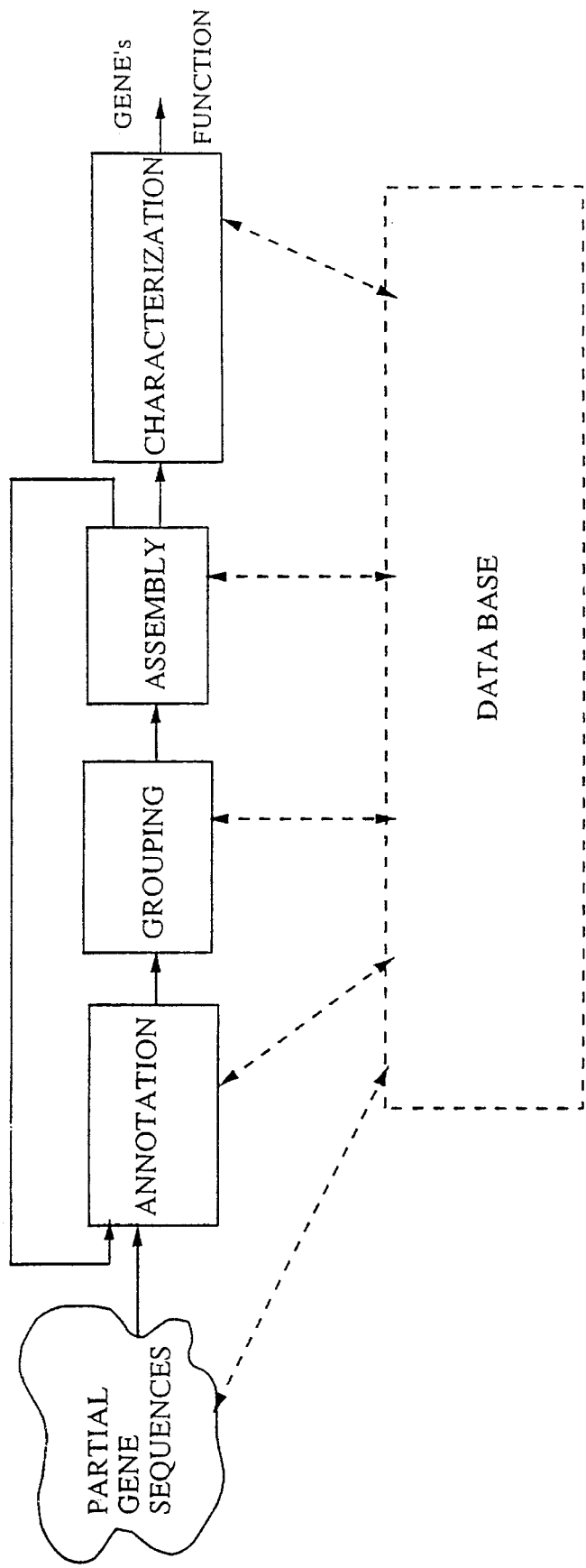
FIG. 1 is a block diagram of an assembly characterization engine for processing partial gene sequences.

The method of the invention provides for automated management of a large and continuously growing population of partial gene sequences. As used herein, the term "partial gene sequences" refers to a series of symbolic codes for nucleotide bases comprising a portion of a gene. Partial gene sequences can be derived by automated or manual methods well known to those skilled in the art and can be stored in a database.

The method is a computer-based iterative process for building putative gene assemblies from a plurality of partial gene sequences. As used herein, "putative gene assembly" is an arrangement of partial gene sequences aligned relative to one another and combined to yield a consensus sequence. The iterative nature of the method of the invention allows for the incremental addition of new partial gene sequences to be integrated with an existing plurality of putative gene assemblies.

Large numbers of partial gene sequences can be assembled by the method of the invention. The gene sequence assemblies produced by the method can be stored in a database and characterized for biological function. The nucleic acids represented by the gene sequence assemblies and the proteins the nucleic acids encode are useful as drug discovery reagents and/or biomedical research tools.

As shown in FIG. 1, the method of the invention broadly comprises three steps of annotation, grouping and assembly. Efficient and accurate assembly of partial gene sequences is achieved through the assembly pre-processing steps of annotating and grouping. The increased efficiency of the present method allows for high throughput of partial gene sequences.

Annotating is a process of identifying regions of partial gene sequences and putative gene assemblies that may cause two unlike sequences to be considered alike. These regions are likely to interfere with the subsequent grouping and assembly steps of the method of the invention. The remaining unidentified regions are considered to contain useful information and are used in the subsequent grouping and assembly steps. Regions identified as likely to interfere with subsequent steps are ignored in those steps.

Examples of regions which can be identified in the annotating step are sequences from contaminating non-species nucleic acids or DNA from cellular structures such as ribosomes and mitochondria. Low information regions which occur multiple times in a genome such as polynucleotide runs, simple tandem repeats (STRs) and repetitive sequences can also be identified. Further, ambiguous regions and regions resulting from experimental error or artifacts are also identified.

After annotation, the annotated partial gene sequences are grouped with other annotated partial gene sequences. The step of grouping the annotated partial gene sequences is based on determining association relationships between an annotated partial gene sequence and other existing annotated partial gene sequences, some of which may be components of previously identified putative gene assemblies. This process begins by ignoring the annotated regions from the partial gene sequences and previously identified putative gene assemblies. The partial gene sequences, with the annotated regions ignored, are then compared with the consensus sequence of previously identified putative gene assemblies, with the annotated regions ignored. The partial gene sequences are also compared with each other, ignoring the annnotated regions. The partial gene sequences are placed in groups based on similarities found in these comparisons. Resulting groups thereby contain a collection of partial gene sequences that would appear to belong together, i.e., the grouping step produces a group of partial gene sequences that are thought to assemble.

For each group from the previous step, the positional ordering of the partial gene sequences relative to one another is taken as a group on the assumption that all partial gene sequences belong to the putative gene assembly. One of the consequences of the ordering may be that more than one putative gene assembly may result should ordering uncover inconsistencies among the group of partial gene sequences.

Once positional ordering has been completed for each putative gene assembly, a consensus sequence is generated by a variety of contig assembly programs known to those of ordinary skill in the art. Exemplary is GELMERGE available from Genetics Computer Group, Inc. in Madison, Wis.

The method of the invention is computer-based. Accordingly, partial gene sequences, annotated partial gene sequences, grouped annotated partial gene sequences and assembled consensus sequences are embodied as signals in a computer while being processed by the method of the invention.

Upon completion of the annotating, grouping, and assembling steps, the putative gene assemblies are stored in a database. Putative gene assemblies may be characterized on the basis of their structure, biological function or other related characteristic. Once categorized, the database can be expanded with information linked to the putative gene assemblies regarding their potential biological function, structure or other characteristics.

For example, one method of characterizing putative gene assemblies is by homology to other known genes. Shared homology of a putative gene assembly with a known gene may indicate a similar biological role or function.

Another exemplary method of characterizing putative gene assemblies is on the basis of known sequence motifs. Certain sequence patterns are known to code for regions of proteins having specific biological characteristics such as signal sequences, transmembrane domains, SH2 domains, etc.

In addition to the methods just discussed, which can be automated, genes may also be characterized on the basis of expert commentary from relevant human specialists for given genes.

It will be apparent to those skilled in the art that various modifications can be made to the present method for analyzing partial gene sequences without departing from the scope or spirit of the invention, and it is intended that the present invention cover modifications and variations of the method for analyzing partial gene sequences provided they come within the scope of the appended claims and their equivalents.

We claim:

1. A computer-based iterative method for building putative gene assemblies from a plurality of partial gene sequences, allowing the incremental addition of new partial gene sequences to be integrated with an existing plurality of putative gene assemblies, comprising the steps of:
    (a) preprocessing the partial gene sequences and existing putative gene assemblies;
    (b) assembling, responsive to grouping relationships, a consensus sequence from the preprocessed partial gene sequences and putative gene assemblies; and
    (c) generating a sequence;
  whereby the preprocessing step allows for efficient and accurate assembly.

2. The method of claim 1 wherein the preprocessing step comprises the steps of:
    (a)(1) annotating regions within each of the plurality of partial gene sequences and each of the plurality of existing putative gene assemblies; and
    (a)(2) grouping annotated partial gene sequences with other annotated partial gene sequences, wherein some of the other annotated partial gene sequences may be components of existing putative gene assemblies.

3. The method of claim 1 further comprising the step of:
    (d) characterizing the consensus sequence.

4. The method of claim 3 wherein the characterization of the consensus sequence is on the basis of homology to known sequences.

5. The method of claim 3 wherein the characterization of the consensus sequence is on the basis of similarities to known sequence motifs.

6. A computer-based iterative method for building putative gene assemblies from a plurality of partial gene sequences, allowing the incremental addition of new partial gene sequences to be integrated with an existing plurality of putative gene assemblies, comprising the steps of:
    (a) annotating regions within each of the plurality of partial gene sequences and each of the plurality of existing putative gene assemblies;
    (b) grouping annotated partial gene sequences with other annotated partial gene sequences, wherein some of the other annotated partial gene sequences may be components of existing putative gene assemblies;

(c) assembling, responsive to grouping relationships, a consensus sequence from the grouped annotated partial gene sequences; and
generating a sequence.

7. The method of claim 6 further comprising the step of:
(e) characterizing the consensus sequence.

8. The method of claim 7 wherein the characterization of the consensus sequence is on the basis of homology to known sequences.

9. The method of claim 7 wherein the characterization of the consensus sequence is on the basis of similarities to known sequence motifs.

10. A computer-based iterative method for building putative gene assemblies from a plurality of partial gene sequences, allowing the incremental addition of new partial gene sequences to be integrated with an existing plurality of putative gene assemblies, comprising the steps of:

(a) annotating regions within each of the plurality of partial gene sequences and each of the plurality of existing putative gene assemblies;

(b) grouping annotated partial gene sequences with other annotated partial gene sequences, wherein some of the other annotated partial gene sequences may be components of existing putative gene assemblies;

(c) assembling, responsive to grouping relationships, a consensus sequence from the grouped annotated partial gene sequences;

(d) characterizing the consensus sequence; and (e) generating a sequence.

* * * * *